(12) United States Patent
Caner (10) Patent No.: US 9,282,957 B2
(45) Date of Patent: Mar. 15, 2016

(54) TABLE ATTACHABLE ADJUSTABLE RETRACTOR SYSTEM

(76) Inventor: Tevfik Cevdet Caner, Istanbul (TR)

( * ) Notice: Subject to any disclaimer, the term of this patent is extended or adjusted under 35 U.S.C. 154(b) by 546 days.

(21) Appl. No.: 13/497,847

(22) PCT Filed: Jul. 1, 2010

(86) PCT No.: PCT/TR2010/000134
§ 371 (c)(1),
(2), (4) Date: Mar. 23, 2012

(87) PCT Pub. No.: WO2011/037548
PCT Pub. Date: Mar. 31, 2011

(65) Prior Publication Data
US 2013/0006060 A1    Jan. 3, 2013

(30) Foreign Application Priority Data
Sep. 24, 2009    (TR) .............................. a 2009 07282

(51) Int. Cl.
*A61B 17/02*    (2006.01)
(52) U.S. Cl.
CPC ......... *A61B 17/0206* (2013.01); *A61B 17/0293* (2013.01); *A61B 2017/0256* (2013.01)
(58) Field of Classification Search
CPC .. A61B 17/0218; A61B 1/32; A61B 17/0293; A61B 17/0206; A61B 17/02; A61B 2017/00991
USPC ................................. 600/201–246; 623/17.16
See application file for complete search history.

(56) References Cited

U.S. PATENT DOCUMENTS

| | | | | |
|---|---|---|---|---|
| 3,572,326 A * | 3/1971 | Jensen | ........................... | 600/233 |
| 4,099,521 A * | 7/1978 | Nestor et al. | ................... | 600/228 |
| 4,116,232 A * | 9/1978 | Rabban | ......................... | 600/215 |
| 4,457,300 A | 7/1984 | Budde | | |
| 4,953,540 A * | 9/1990 | Ray et al. | ....................... | 600/233 |
| 5,849,004 A * | 12/1998 | Bramlet | ......................... | 606/232 |
| 6,315,718 B1 | 11/2001 | Sharratt | | |
| 7,179,262 B2 * | 2/2007 | Bryan et al. | ..................... | 606/79 |
| 7,326,249 B2 * | 2/2008 | Lange | .......................... | 623/17.11 |
| 7,887,482 B2 * | 2/2011 | Hamada | ......................... | 600/233 |
| 8,617,245 B2 * | 12/2013 | Brett | ............................. | 623/17.16 |
| 8,968,192 B2 * | 3/2015 | Protopsaltis | ................... | 600/219 |
| 2004/0059193 A1 | 3/2004 | Fanous | | |
| 2004/0073214 A1 * | 4/2004 | Mehdizadeh | ..................... | 606/61 |
| 2004/0153089 A1 * | 8/2004 | Zdeblick et al. | ................. | 606/90 |
| 2005/0192484 A1 | 9/2005 | Sharratt | | |
| 2006/0084843 A1 * | 4/2006 | Sommerich et al. | ........... | 600/210 |
| 2008/0200987 A1 * | 8/2008 | Copf, Jr. | ....................... | 623/17.16 |
| 2011/0301420 A1 * | 12/2011 | Pryor et al. | ....................... | 600/207 |

FOREIGN PATENT DOCUMENTS

EP    1642536 A2    7/1984

OTHER PUBLICATIONS

International Search Report for corresponding International Application No. PCT/TR2010/000134.

* cited by examiner

*Primary Examiner* — Jerry Cumberledge
(74) *Attorney, Agent, or Firm* — Egbert Law Offices, PLLC (57) ABSTRACT

A novel retractor system can be attached to a table and can be adjusted at desired points in x-y-z axes, and which provides spine surgeries be made in a healthier manner via retractors which are mounted on the retractor carrier wings, and a set, which provides fusion of spines via this system by using an insert.

6 Claims, 10 Drawing Sheets

TABLE ATTACHABLE ADJUSTABLE RETRACTOR SYSTEM

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to table attachable retractor and fusion set which is used for eliminating spine disorders in spine treatments of people.

The invention particularly relates to a novel retractor system, which can be attached to table and can be adjusted at desired points in x-y-z axes, and which provides spine surgeries be made in a healthier manner via retractors which are mounted on the retractor carrier wings, and a set, which provides fusion of spines via this system by using an insert.

2. Description of Related Art Including Information Disclosed Under 37 CFR 1.97 and 37 CFR 1.98.

Nowadays, many spine disorders occur due to various reasons. Most of these spine disorders are mechanical and they are tried to be treated' by surgical methods. In order to perform surgery on the spine, the region of surgery has to be clearly visible. The chance of success of the surgery would decrease in case the mechanical elements and details are not clearly visible.

Related with the retractors, patent applications are found with no US2002026101, U.S. Pat. No. 5,429,121, and WO2007085909. However, some problems are found in the solutions presented by these applications. Their positions can not be adjusted since they are not fixed to the operation table. Therefore it is both difficult to see the region of surgery adequately and to adjust the position of the retractor according to the patient. Because of these reasons, the surgical operations become harder.

A good field of view is necessary for these purposes: Since the' tools used during operation occupy a lot of place, the region of surgery can not be seen in a very clear way. While fixing other surgical tools to the spine by separating muscles, dislocations may occur. In case of dislocation of these tools, spine and muscles may be harmed.

While remounting them, the region of surgery may be harmed. Moreover, when peroperative x-ray is used, the retractor attached to the table should, not obstruct the sight.

In lumbar disc surgery, most of the time simple diskectomy is conducted and fusion operations are not added. During surgery, annulus at the region of herniation can be weak and torn due to disease, and it is also surgically cut and opened.

No matter how well the disc is cleaned, recurrent disc (disc formation again) may occur. Since placement of an insert between the spine distance, on which surgery is performed, would prevent both spines from getting close to each other, re-formation of high pressure at the disc distance would be prevented. The covers fitting on the inserts used in other fusion surgeries only fit on the inserts and the do not comprise the cut parts of the posterior band. Therefore recurrence may occur from the gaps found at the posterior band. This situation has to be prevented.

In summary, the problems and their solutions are;

1. Presence of an insert would prevent narrowing of the interspace and prevent disintegration of the disc by preventing re-increase of disc distance pressure and thus the possibility of migration of the disc would be eliminated.

2. The possibility of unstable (mobile spine), which would lead to post operative problems, has to be decreased.

3. A structure is needed, in which the cover extending toward line below the posterior band by being fixed on the insert, both eliminates the recurrence possibility, helps stabilization of the insert, and prevents the bone parts placed at the interspace used for fusion reach the epidural distance.

In treatment of spondylolisthesis, spines are located by placing screw to spine corpuses from the pedicules and thus being pulled and attached to the rods. In this case, although the disease is only between two spines, for fixing, a distance up to two spines each upwards and downwards is opened and operation is also made on healthy muscles and pedicules. And these interventions made on healthy regions cause iatrogenic morbidity and lead to "Failed back" syndrome.

A novel retractor system, which provides elimination of problems occurring in the said operations, and improvement of treatments made by this system are needed.

BRIEF SUMMARY OF THE INVENTION

From the known status of the art, the purpose of the invention is to develop a novel table attachable and adjustable retractor system, which eliminates the drawbacks of the prior embodiments and brings about many advantages, and a fusion set used with this retractor system.

Another purpose of the invention is to increase workspace and thus form better excluded operative fields.

Another purpose of the invention is to provide adjustment of the position of the face to face positioned retractor carrier wings by fixing them to the table.

Another purpose of the invention is to provide opening of the operative field by mounting the retractors on the housing formed on the retractor carrier wing.

Another purpose of the invention is to provide adjustment of the position of the retractor, so that it can be easily adjusted during surgery according to the patient.

Another purpose of the invention is to provide elimination of all mechanical disorders occurring in the spine without harming adjacent tissues.

Another purpose of the invention is to prevent tools from sliding but of the retractors during operation, as it occurs in other retractor (muscle separating) systems, and thus reduce the possibility of the traumatisation of adjacent tissues. Purpose is to prevent time losses. Purpose is not to lose the positions found during operation.

Moreover, these operations are harmful on muscle tissues. Another purpose is to provide elimination of these problems:

Another purpose of the invention is to ensure performing mechanical surgery operations in an easier way by providing a retractor system, which can be mounted and de-mounted, and in which position adjustment could be made at various points.

Another purpose of the invention is to provide the separator components to be separable from the separator edge releasing point formed on itself by the releasing apparatus.

Another purpose of the invention is to provide adjustments be easily made in sterile conditions in the desired x-y-z positions during surgery.

Another purpose of the invention is to provide easy elimination of problems which occur during operations made on spine.

In order to achieve the said purposes, a novel retractor system, which can be mounted and de-mounted, and in which the facilities for easy adjustment of x-y-z positions are provided at various points and in sterile conditions.

A preferred application of the invention, in order to form a retractor system which is positioned on the operation table and position of which can be adjustable at desired points, comprises: at least two face to face positioned retractor carrier wings which are fixed to the table and which provide adjustment of position at desired points according to the patient and intervention to the spine by separating muscles, retractor carrier wing bodies which form the retractor carrier wings, and at least one separator component (4), which is positioned on the separator component housing (3) formed on the retractor carrier wing bodies (2) in a way that it could be mounted and de-mounted, and axial position of which can be adjustable according to patient and the table.

In a preferred application of the invention, at least one retractor carrier wing position adjustment component and/or retractor carrier wing position adjustment housing are formed, by which the position of both two retractor carrier wings are adjusted at y axis.

A preferred application of the invention comprises at least one side arm, which provides connection of the said retractor carrier wing to the table, and position of which is adjustable in y axis, at least one body connection arm, to which the side arm is connected, and which has a structure such that its position can be adjustable, and at least one body, which is connected to the body connection arm, and which is formed in order to be fixed to the table.

A representative application of the invention comprises at least one body connection arm housing, to which the body and the body connection arm are connected.

In a preferred application of the invention, at least one table connection is formed on the body, which provides fixation on the table.

In a preferred application of the invention, between the side arm which is connected to the said retractor carrier wing, at least one retractor carrier wing y-z axis position adjustment component (8) is formed, which provides adjustment of the position of the retractor carrier wing in y-z axis.

A preferred application of the invention comprises a side arm which has a position adjustable structure such that it can be opened and closed telescopically.

A preferred application of the invention comprises retractor carrier wing position adjustment component, position of which is fixed by being adjusted via the fixing component and by moving inside the retractor carrier wing position adjustment component housing.

In a preferred application of the invention, at least one retractor carrier wing-separator component connection part is formed on the separator component, and it provides the separator components be mounted on the separator component housing found on the retractor carrier wing body.

A preferred application of the invention comprises a separator component position adjustment point formed on the retractor carrier wing-separator component connection part, and at least one separator component position adjustment housing, desired position of which is adjusted from the separator component position adjustment point.

A preferred application of the invention comprises at least one separator edge which is formed on the separator component.

In a preferred application of the invention at least one separator edge releasing point is formed, which provides separation of the separator edge part when required.

A preferred application of the invention comprises at least one separator edge y-z axis adjustment point which provides adjustment of the position of the separator edge part in y-z axis.

In a preferred application of the invention at least two face to face positioned lateral holder components are formed on the separator edge, and at least one separating tool is formed on the lateral holder components.

A preferred application of the invention comprises at least one lateral holder component assembly extension which is formed on the said lateral holder components, at least one screw component which is positioned inside the lateral holder component assembly extension, at least one lateral holder component assembly extension housing in which the screw component and the lateral holder component assembly extension are positioned on the separator edge, and at least one separator edge y-axis adjustment point, which is connected to the screw component inside the lateral holder component assembly extension, and in which the position of the separating tools can be adjusted in y axis.

In a preferred application of the invention at least one separator edge z-axis adjustment point is formed, by which the position of the said separating tools are adjusted on the lateral holder component in z axis, and a screw component is formed on the separating tool which is connected to the screw component formed on the separator edge z-axis adjustment point.

A preferred application of the invention comprises a fixing apparatus, by which its position is fixed at the separator component position adjustment point found on the separator component, and a releasing apparatus, by which the separator edge part is released from the separator edge releasing point found on the separator component and thus the means of operation is provided.

In a preferred application of the invention, in order to provide operation in smaller areas, it comprises engaging into each other from the protrusions and recessions found on the said separating tools, combining into a smaller structure and then performing operations on the spine by being separated.

In a preferred application of the invention, in the mechanical operations made on spine with the separator components found on the retractor carrier wing body, the relevant part is covered by a cover component after disc cleaning, implant between spines and insertion of the insert.

A preferred application of the invention, in order to be used in spondylolisthesis and herniated disc treatments, comprises an insert, which is mounted between the two spines, having disc cleaning completed, via the insert positioning and fixing component, an insert fixing tool which makes fixing operation through the spine by passing on the spine by passing through the housings formed inside the insert, and an insert positioning and fixing component which provides positioning of the insert fixing tool.

A preferred application of the invention comprises at least one leaning surface, which provides its leaning on the disc surface in a certain distance on the said insert positioning and fixing component.

In a preferred application of the invention at least one cover component is formed, which covers both two sides of the spine with complete sealing by being coupled on the said insert. This cover component prevents axial movements by strengthening the posterior band and making the insert more stabile.

A preferred application of the invention comprises a housing which is formed on the insert in a way that it lays in a vertical position with the spine, and an insert fixing tool which passes through the housing.

A preferred application of the invention comprises at least one disc puller component, which is formed in order to bring the spine again to its physiological position in spondylolisthesis, and at least one positioning apparatus, by which the position of the disc puller component is adjusted.

In a preferred application of the invention at least one positioning apparatus is formed, which provides removal or position adjustment of fixing tools found on the disc puller component and insert positioning and fixing component, and a rotation component, by which the required movement is controlled manually in the positioning apparatus.

A preferred application of the invention comprises the operation steps of formation of at least two face to face retractor carrier wings, which are fixed on the table, and which provide adjustment of its position at desired points according to the patient and which provide intervention on the spine by separating muscles, positioning of at least one separator component in a way that, the retractor carrier wing bodies forming the retractor carrier wings are positioned on the separator component housing formed on the retractor carrier wing and axial position of which can be adjusted according to the patient and the table, and/or bringing the position of the spine to its physiological position via the disc puller component, by which the relevant operations are made in the region of surgery separated by the separator components, and which is mounted to the spines only by the diseased interspace for slipped discs, and/or fixation of the insert to the spines via fixing tools by positioning an insert between the two cleaned spines in the disorders of herniated disc and/or spondylolisthesis, and covering both sides of the insert in a sealed manner by the cover component.

In a preferred application of the invention, in case of spondylolisthesis, it comprises fixation of the fixing tools, found on the spine puller component, to the spine using positioning apparatus with the bearing point over the retractor carrier wing body of the spine puller component, and by adjusting its position, bringing the spine to its physiological position. Moreover, in order to place the permanent inserts, the spine puller component is also removed with a movement which is opposite to fixation.

In a preferred application of the invention, when it is required to provide engagement of the fixing tools, which are mounted to the housings on the insert, to the spine with a certain angle via the insert positioning and fixing component by pressure force at one point and provide removal of it again, it comprises removal of the fixing tools from their places in order to remove the insert from its place via the positioning apparatus.

In a preferred application of the invention, fixation of fixing tools to the spine is made by mounting them into the insert via the positioning apparatus assembly component, and covering it with the cover component having a longitudinal structure, and in order to provide removal of insert when required, it comprises removal of the cover component, and pulling of the fixing tools by being turned from inside the positioning apparatus via the rotation components which are connected to the screwed extension found on the position adjustment component which are connected to the fixing tools found on the insert.

In a preferred application of the invention, the lower and upper openings of the two inserts (34), which are mounted between the two spines (41) from two sides, are covered in a sealed manner via the cover component (37) which is fixed with the fixing holes (52) by being mounted at the fixing points (51) found on the insert (34).

In a preferred application of the invention, it has a telescoping structure in order to provide separation with a more sensitive structure and in, a smaller area in entrance between the two spines (41) with a vertical position with the muscles and the nerves by an adjustment of the x-y-z position made from the relevant adjustment points (21, 22, 23) during the operation via the said separating tool (24), in which its position is adjusted according to the patient and the table.

REFERENCE NUMBERS

1 Body
2 Retractor carrier wing body
3 Separator component housing
4 Separator component (retractor)
5 Retractor carrier wing
6 Retractor carrier wing position adjustment component
7 Retractor carrier wing position adjustment component housing
8 Retractor carrier wing y-z axis position; adjustment component
9 Retractor carrier wing y axis position adjustment component
10 Side arm
11 Side arm position adjustment component
12 Side arm fixing component
13 Body connection arm position component
14 Body connection arm
15 Body connection arm housing
16 Table connection
17 Separator component position adjustment point
18 Separator component position adjustment housing
19 Retractor carrier wing-separator component connection part
20 Separator edge releasing point
21 Separator edge y-z axis adjustment point
22 Separator edge y-axis adjustment point
23 Separator edge z-axis adjustment point
24 Separating tool (pin etc.)
25 Fixing component
26 Screw component
27 Lateral holder component
28 Adjustment component housing
29 Separator edge
30 Lateral holder component assembly extension
31 Lateral holder component assembly extension housing
32 Fixing apparatus
33 Releasing apparatus
34 Insert (locating implant)
35 Fixing tool
36 Housing
37 Cover component
38 Leaning surface
39 Insert, positioning and fixing adjustment component
40 Pusher component
41 Spine
42 Rack gear
43 Positioning apparatus
44 Rotation component
45 Bearing point
46 Spine puller component
47 Assembly component
48 Articulated connection
49 Screwed extension
50 Position adjustment component
51 Fixing point
52 Fixing hole

DETAILED DESCRIPTION OF THE INVENTION

A novel retractor system is developed for spine surgeries, which can be mounted and de-mounted and which provides the opportunity of being easily adjusted.

Figure 1:
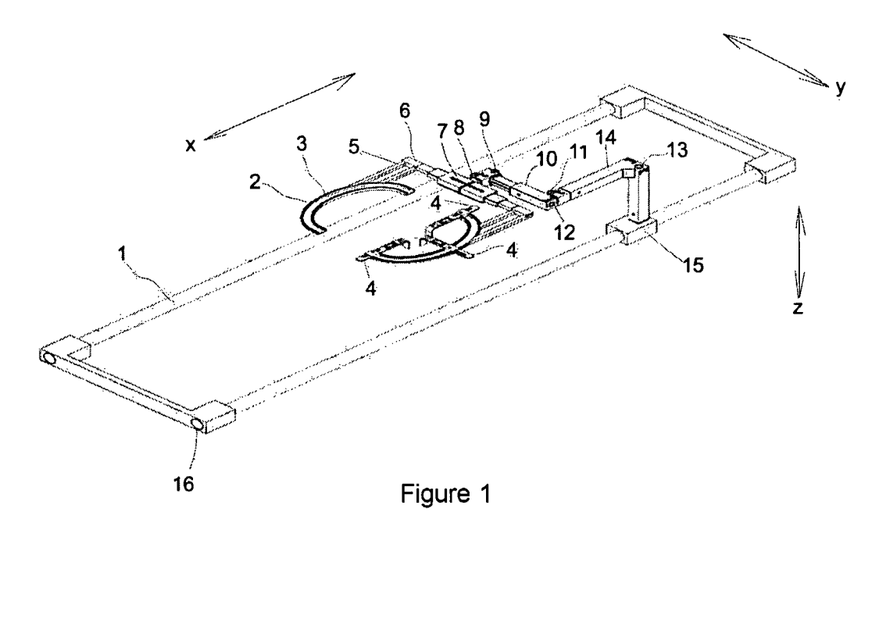
FIG. 1 is a perspective drawing which shows a representative application of the invention.

As it is seen in FIG. 1, table connections (16) are found on the body (1) which is formed in order to be mounted to the table. On the body (1), which is fixed on the table connections (16), a body connection arm (14) is found, which is connected from the connection arm housing (15). The desired position can be adjusted using the body connection arm position adjustment component (13).

The side arm (10), which is connected with the body connection arm (14), is positioned. The desired position adjustment is made using the side arm position adjustment component (11). With the side arm fixing component (12) and the retractor carrier wing y axis position adjustment component (9), a side arm (10), having a structure which can be opened and closed, is formed and its positioned can be adjusted. The retractor carrier wing position adjustment component (6), which is connected with the retractor carrier wing y-z axis position adjustment component (8), adjusts the position of the retractor carrier wing (5) and the retractor carrier wing body (2) by moving in the retractor carrier wing position adjustment component housing (7). Multiple separator components (4) found on the retractor carrier wing body (2) are positioned by being mounted to the separator component housing (3).

Figure 2:
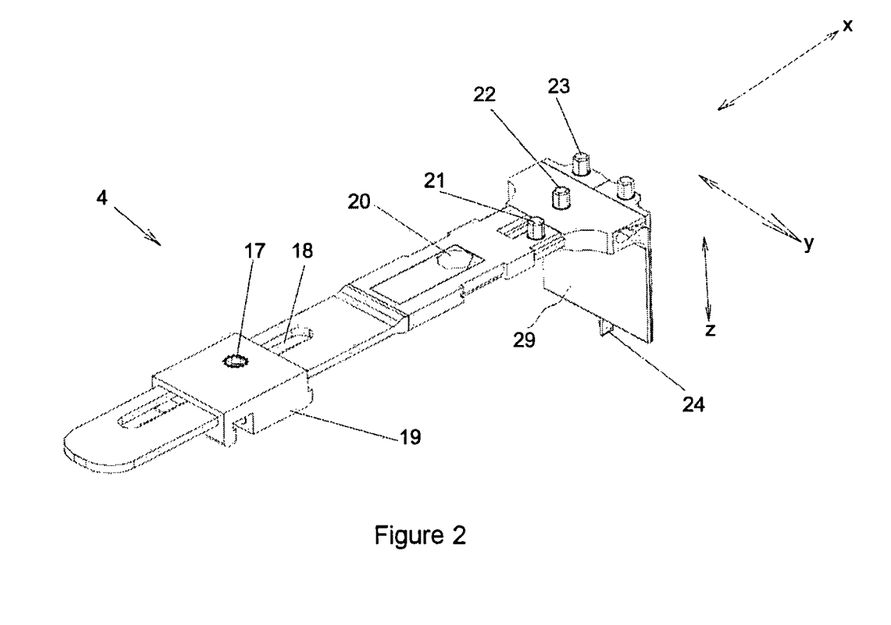
FIG. 2 is a drawing which shows the separator component in a representative application of the invention.

As it is seen in FIG. 2, the separator component (4) moves in the separator component position adjustment housing (18) from the separator component position adjustment point (17), and it is fixed at a certain position on the retractor carrier wing-separator component connection part (19). The separator edge (29) part can be separated from the separator edge releasing point (20). At the separator edge (29) part, the separator edge y-z axis adjustment point (21), the separator edge y axis adjustment point (22), and the separator edge z-axis adjustment points (23) are formed. The z axis (upwards and downwards) position of the separating tool (24) found on the separator edge (29) is adjusted from the separator edge z-axis adjustment point (23).

Figure 3:
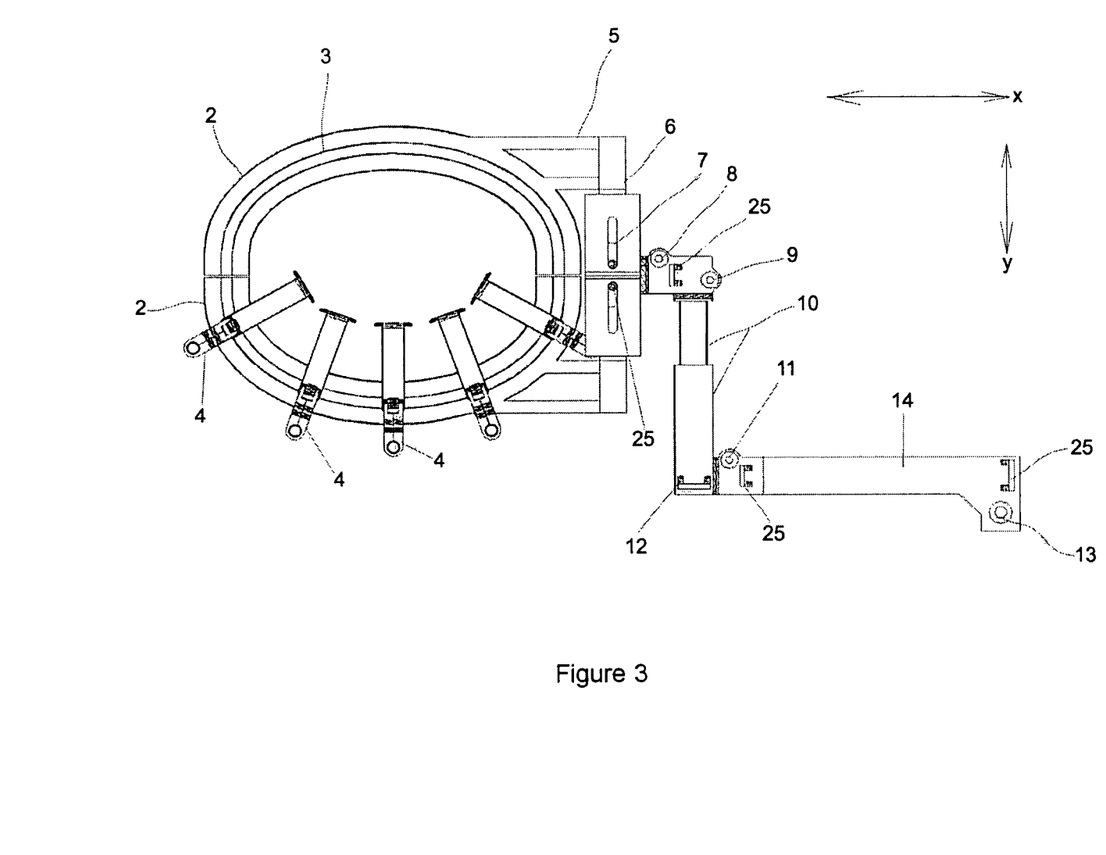
FIG. 3 is a drawing of the top view of a representative application of the invention.

As it is seen in FIG. 3, the body connection arm (14), the fixing components (25) found on the side arm (10), and the side arm fixing components (12) are fixed by adjustment of their positions in x and y axis in screw form. With the fixing component (25) found in the retractor carrier wing position adjustment component housing (7), the y axis position of both two retractor carrier wings (5) and the retractor carrier wing body (2) are adjusted. The required operations are made via the separator components (4) mounted on the separator component housings (3) found on the retractor carrier wing body (2).

Figure 4:
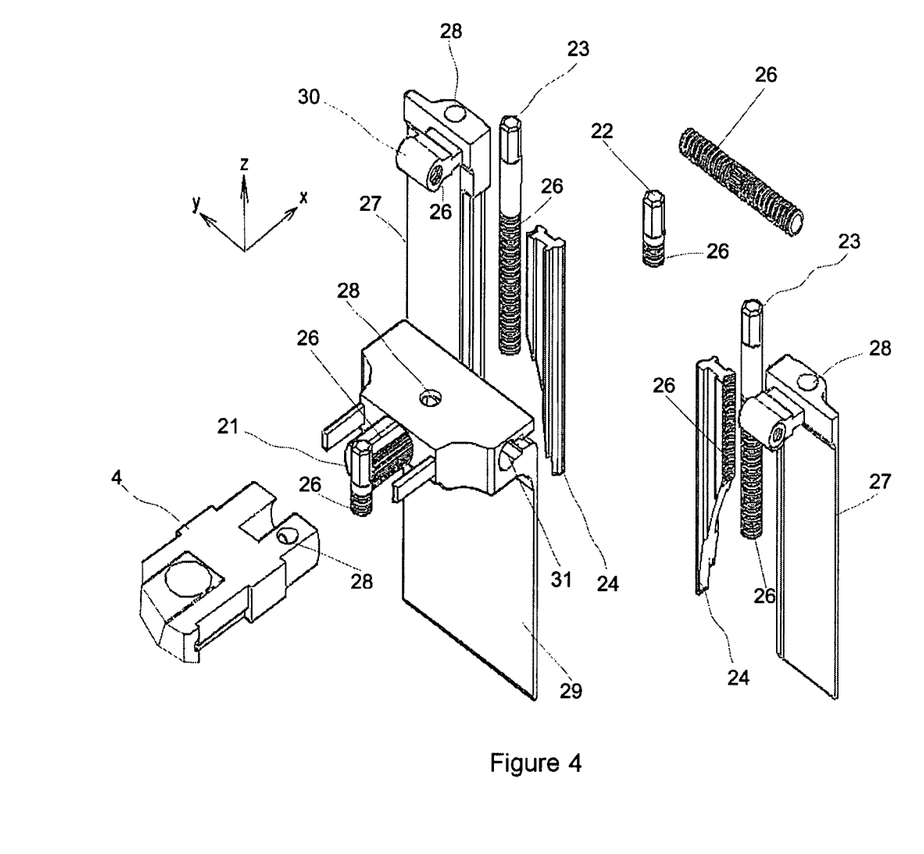
FIG. 4 is a drawing of the demounted perspective view of the separator edge part found on the separator component in a representative application of the invention.

As it is seen in FIG. 4, on the separator edge (29), the lateral holder component assembly extension housing (31), the adjustment component housing (28), and the screw component (26) are positioned. The screw component (26) is found on the separator edge y-z axis adjustment point (21), which is connected with the screw component (26). In this way, the separator edge (29) y-z axis position, in other words, the pandular movement can be adjusted. Inside the adjustment component housing (28) found on the separator component (4), the separator edge y-z axis adjustment point (21) is positioned. 1 In the adjustment component housing (28) found on the lateral holder components (27) mounted on the separator edge (29), the separator edge z axis adjustment point (23) is formed. With the screw component (26) found on the separator edge z axis adjustment point (23) and the screw component (26) part found on the separating tool (24), the upwards and downwards movement of the separating tool (24) is provided in z axis. From inside of the lateral holder component assembly extensions (30), which are mounted to the lateral holder component assembly extension housing (31), the screw component (26) passes, and the separator edge y axis adjustment point (22) is connected through the adjustment housing (28). The separator edge y axis adjustment point (22) is turned via the screw component (26) part found in itself, and the y axis positions of the separating tools (24) are adjusted together with the lateral holder components (27). Separating tools (24) are mounted on both two lateral holder components (27).

Figure 5:
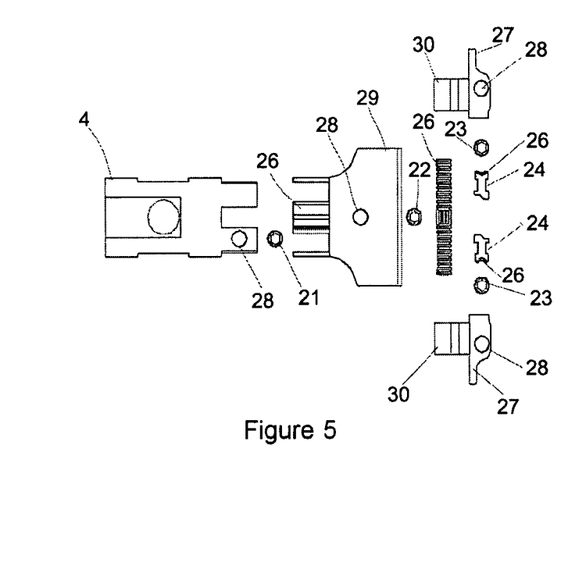
FIG. 5 is a drawing of the demounted top view of the separator edge part found on the separator component in a representative application of the invention.
Figure 6:
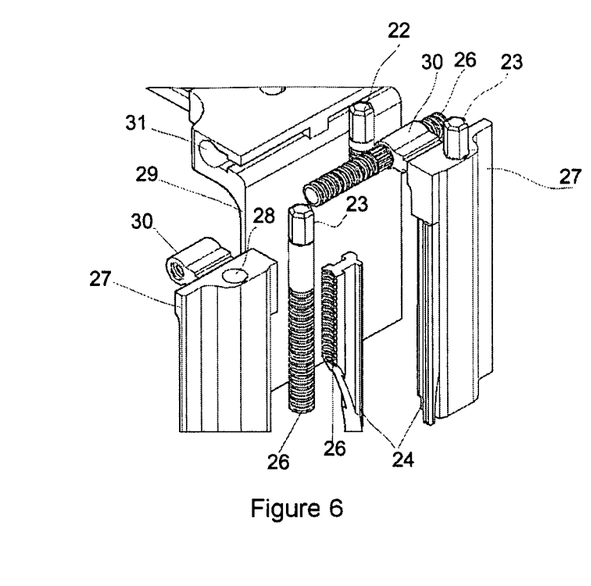
FIG. 6 is a drawing of the demounted front perspective view of the separator edge part found on the separator component in a representative application of the invention.

As it is seen in FIG. 5 and FIG. 6, the separating tools (24) are mounted on the lateral holder components (27) and its position is adjusted from the; separator edge z axis adjustment point (23). From the separator edge y axis adjustment point (22) on the screw component (26) which is mounted inside the lateral holder component assembly extension (30) found on the lateral holder components (27), its position is adjusted from the lateral holder component assembly extension housing (31).

Figure 7:
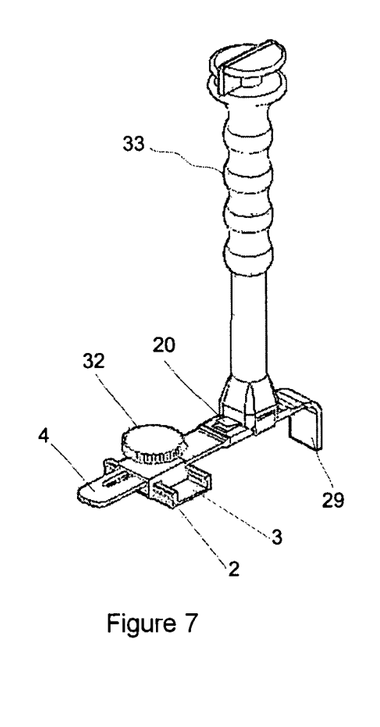
FIG. 7 is a drawing which shows separation of the separator edge part found on the separator component by the separator apparatus in a representative application of the invention.
Figure 8:
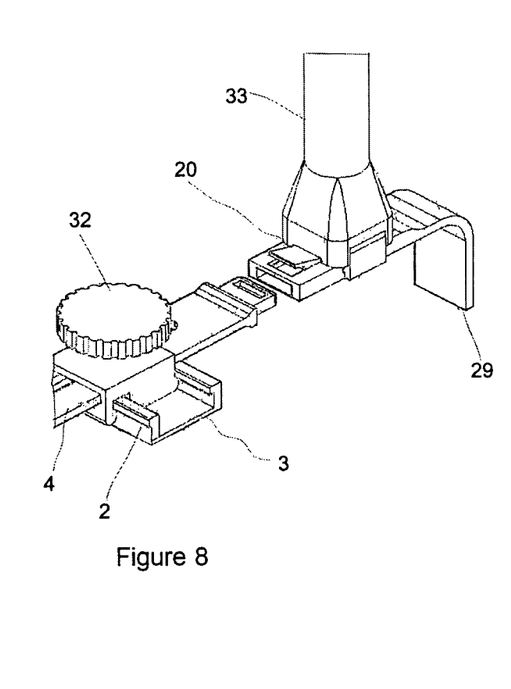
FIG. 8 is a drawing which shows the situation in which the separator edge part found on the separator component is separated by the separator apparatus in a representative application of the invention.
Figure 9:
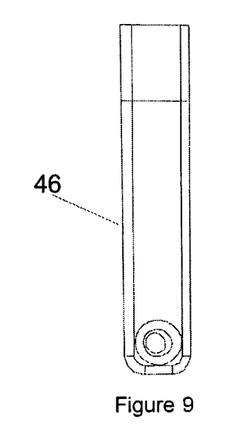
FIG. 9 is a drawing which shows the spine puller component in a representative application of the invention.
Figure 10:
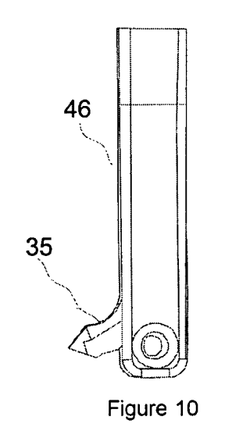
FIG. 10 is a drawing which shows the ejection of the fixing tool out of the spine puller component in a representative application of the invention.
Figure 11:
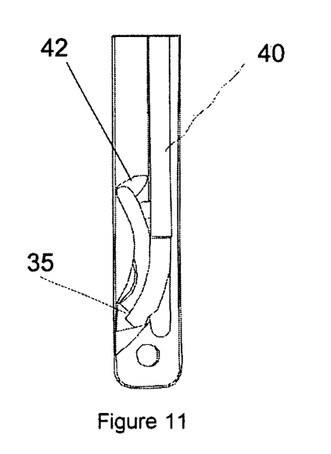
FIG. 11 is a drawing which shows the fixing tool which is associated with the spine puller component in a representative application of the invention.
Figure 12:
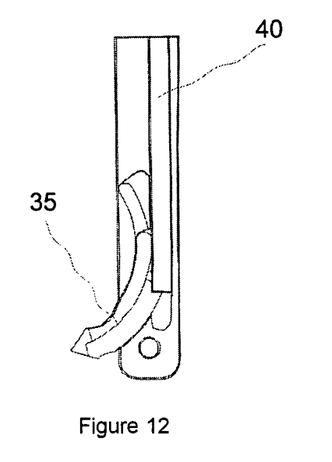
FIG. 12 is a drawing which shows the ejection location of the insert fixing tool at the inner part of the pusher component body in a representative application of the invention.

As it is seen in FIG. 7 and FIG. 8, the separator component (4) is fixed at the separator component position adjustment point (17) found on the retractor carrier wing body (2) via the fixing apparatus (32). The separator edge (29) part can be removed from the separator edge releasing point (20) via the releasing apparatus (33).

As it is seen in the figures between FIG. 9 to FIG. 17, in the disorders of spondylolisthesis and herniated discs, after cleaning the area between the two spines (41), an insert (34) is placed between. As it is seen in the figures between FIG. 13 to FIG. 15, insert fixing tools (35) are formed by passing over the insert positioning and fixing component (39), and through the housings (36) in a vertical position with the spines (41). The insert (34) is placed between two spines (41) with the insert positioning and fixing component (39).

Figure 13:
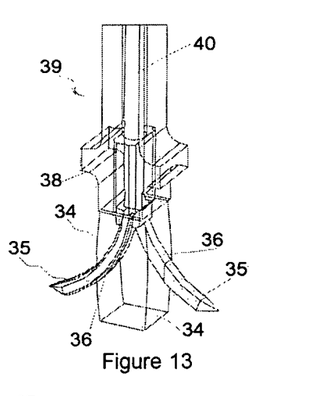
FIG. 13 is a drawing which shows the mounted form of the insert and the insert positioning and fixing component between two spines in a representative application of the invention.
Figure 14:
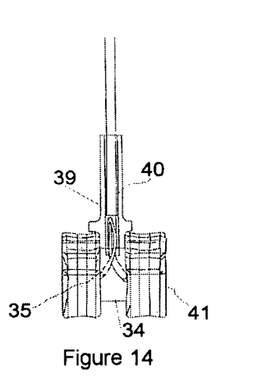
FIG. 14 is a drawing which shows the mounted form of the insert fixing tool to the discs from the inner part of the insert via the pusher component in a representative application of the invention.
Figure 15:
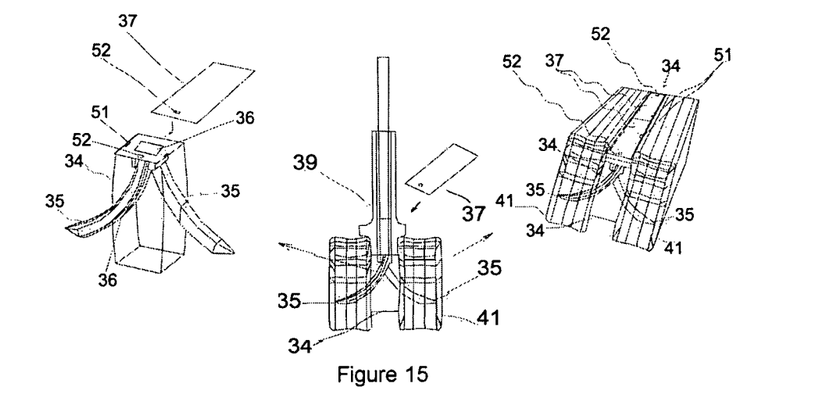
FIG. 15 consists of the drawings in which a completely closed form of the said insert and the cover component found on it and the fixing tools, which are completely attached to the spine by passing through the housing found inside the insert, are shown in a representative application of the invention.

As it is seen in FIG. 13, the leaning surface (38), found on the insert positioning and fixing component (39), provides positioning up to a certain distance on the spine (41). And the possibility of harming the front organs by slipping from its place is eliminated. The fixing tool (35), which is connected with the pusher component (40) through the insert positioning and fixing component (39), enters the spine (41) endplates from the housing (36) found inside the insert (34) with a vertical position and thus provides fixing. As it is seen in FIG. 15, two cover components (37) cover between the two spines (41) in a sealed manner and pass from the fixing points (51) found on the insert (34) and thus are fixed from the fixing holes (52). Fixing points (51) provide fixation of the cover component (37) without being removed. In this way, slipping of two spines (41) again or compression of nerve roots again in the foremen due to narrowing of disc distances are prevented.

Figure 16:
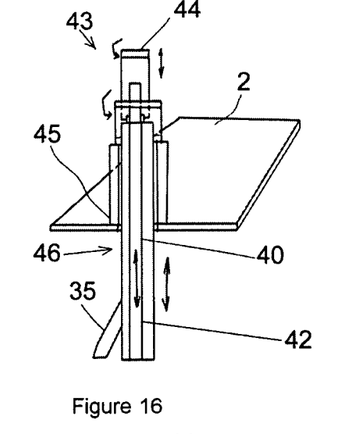
FIG. 16 is a drawing which shows the way in which the spine puller component brings the spine in its physiological position via the positioning apparatus through the retractor carrier wing body in a representative application of the invention.

Moreover, as it is seen in FIG. 16, the fixing tool (35) found on the spine puller component (46) is fixed on the spine and thus provides the spine (41) be brought to its physiological position from the point it slipped. For this purpose, the positioning apparatus (43) is used, which is connected to spine puller component (46). Positioning apparatus (43) provides pulling of the spine puller component (46) from the bearing point (45) in a certain distance by rotation of the rotation component (44).

Figure 17:
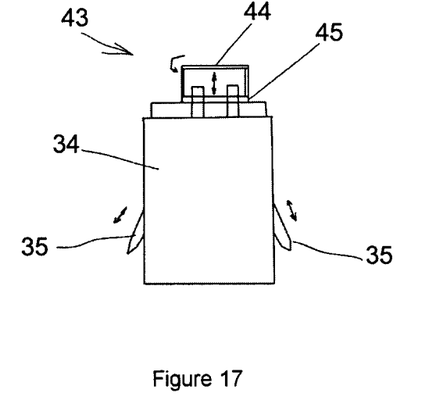
FIG. 17 is a drawing which shows the way in which the fixing tools found on the insert are ejected via the positioning apparatus in a representative application of the invention.

As it is seen in FIG. 17, on the insert positioning and fixing component (39), by using the positioning apparatus (43), the fixing tools (35) are removed from the bearing point (45) with the rotation component (44) when required. The rotation component (44) connected with the fixing tools (35) is manually rotated and thus provides removal of fixing tools (35) in a certain rotation distance.

Figure 18:
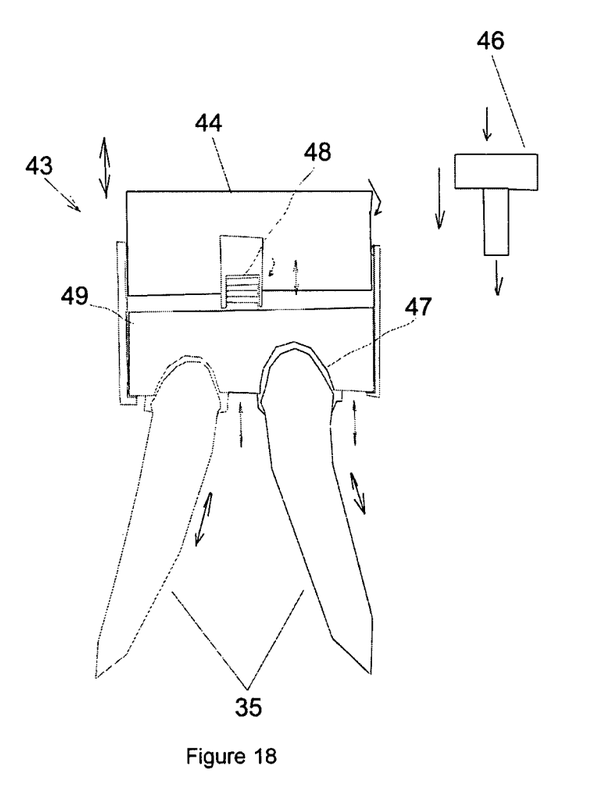
FIG. 18 is a drawing which shows the way in which the fixing tools of the positioning apparatus are inserted into and/or ejected out of the insert in a representative application of the invention.

As it is seen in FIG. 18, a sample positioning apparatus (43) is given, which is formed for mounting of the fixing tools (35) to the housings (36) found inside the insert (34). With the positioning apparatus (43) and the articulated connection (47), the fixing tools (35) are connected to the position adjustment component (49).

The rotation component (44) is mounted on the screwed extension (48) found on the position adjustment component (49) and then it is locked. Afterwards, since the position adjustment component (49) is free, the rotation component (44) is rotated inside the positioning apparatus (43) and pulled upwards. In this way, the fixing tools (35) are removed and insert (34) is left free.

Again, when the insert (34) is mounted, the fixing tools (35) are pushed downwards via the assembly component (46) over the screwed extension (48) found on the position adjustment component (49), and thus fixed. Since the fixing tools (35) are free in their own axis thanks to the articulated connection (47), it can be removed without harming the spine in mounting and demounting operations. Similarly, fixation and removal of the insert (34) is provided in different ways.

Disclosure of Exemplary Applications

The said retractor system of ours is such as system that, it has tens of large and small parts in it. With these parts, it provides the possibility of performing operation from the front side and the backside.

Our purpose here is to provide a more clear vision of the region of surgery in surgical disorders occurring in the spine. Retraction is made in order to reach the region of surgery. The better the region of surgery is seen, the better would the surgery be performed.

The better the pathologies of the disorders are shown, the better results would be obtained in having the most suitable solutions and applying them.

By separating the muscles in a good way, a good vision is provided. The inadequacy in the known applications is because of the separation operation of the muscles causing deformation of the muscles. The tool slips and gets out of its place. Its re-mounting is difficult. While bleeding may occur during re-mounting of the tool to its place, it also causes loss of time and orientation.

In order to prevent these, the retractor is mounted to the operation table.

In the known applications, when the operation table is fixed, movement of the patient or the table is difficult, since they are both fixed. Therefore, a fixed structure is obtained.

There are similar structures which are fixed to the operation table. However, their adjustment (change of position) is difficult during surgery. Their usage is also difficult. This situation both affects the surgery and a precise adjustment can not be made. However, in our invention, the adjustments of the arms (5,10,14) found on the body (1) extending from the table are easily made (in x, y, z coordinates) in sterile conditions with a screwdriver. It provides the facility of making easy adjustment by intervening from a single point and prevents loss of time.

The operation field can be fixed to the half retractor carrier wing (5) coming towards itself, but the movable separator components (retractor pullers) (4) and patterns of these (in adjustable structure) can be mounted to the retractor carrier wing body (2). These tools can be mounted and de-mounted in a very easy manner.

The separator edges (retractor edges) (29) can be used in different structures according to the patient. Moreover, the separator edges (retractor edges) (29) can be adjusted by pandular (z-y axis) in order to be placed just across the operation field according to the patient or the table. In this separator edge (29) 2 separating tools (pins) (24), depth of which can be adjusted, are found. Between the spines, the said separating tools (pins) (24) are opened and thus the distance of the spines are opened. And we can make corpus vertebra retraction to this. Therefore, we can easily insert the tools between the disc opening and work there. And visual areas are obtained which are suitable for micro surgery. The required inserts (34) are easily placed.

After the Diskectomy (cleaning of the disc) is made, a specially produced locating implant (34) is placed between the two spines (41), opening of which is separated. The property of this implant (34) is being placed in one movement and a special screwing system (fixing tools (35)) coming out of the implant (34) fixes the implant (34) to the corpus vertebra (34) at both upper and the lower vertebra. Furthermore, the shape of the implant (34) is convenient with the slopes found in the disc distance. Via the slopes and the screw system coming out of the implant, this part provides great easiness and use of other spines (41) are not needed with only one movement.

Problems in similar systems are making unnecessary instrumentation on healthy spines (41) because of the need for using healthy spines (41). The used instruments causing morbidity on the places which are healthy before the surgery, and the performed excessive paravertebral dissection causing negative impacts on stabilization. As a result of placement of the insert (34), the pressure found at the interspace does not raise. The insert (34) is between two vertebras. It prevents the vertebra from coming close to each other. In order to prevent re-formation of disc, such a cap is placed that, the opened and weak part of the posterior band has to be closed. In the prior applications, a cover (cap) component (37) is not found, which can close here longitudinally. Furthermore, with the insert (34), this cover (37) prevents narrowing of interspace and increase of pressure. The spine distance is kept constant with the insert (34) placed between. Moreover, thanks to the cover (37) closing the opened area, formation of recurrent disc due to the disc getting out of there again is prevented. Implantation is made as a strong barrier for prevention of recurrent disc. And, if bone parts are used for fusion, outpouring of these to the epidural distance can be prevented.

Treatment related with spine (41) spondylolisthesis is as follows.

In the treatment of spondylolisthesis, bringing the spines (41) to their physiological places and their fixation has difficulties. In the known applications, treatments are made on healthy spines (41) by using screws via pedicules. In this case, healthy spines are used in order to treat the diseased place and morbidity of lower and upper distances of healthy spines occur. All of these result from performing operation in a larger area. Significant risks are in question due to harming of the healthy spines (41). And while the diseased parts are being treated, iatrogenic problems may occur related with the healthy places.

In the said retractor system of ours, operation is performed only on the diseased spine (41). This is made via the retractor system which is fixed to the table and mounted in an adjustable structure. As in the first described application, it is mounted on the retractor carrier wing body (2) which is mounted to the retractors. Following the diskectomy (cleaning of the disc), the separator components (retractors) (4) mounted to the table are fixed to the retractor carrier wing body (2) and a spine puller component (46) is found which is mounted to the retractor carrier wing body (2). The property of this spine puller component (46) is:

The spine puller component (46) can be adapted to the disc distance in terms of thickness and shape. Moreover, via the toothed rack system found in itself, the fixing tool (35) which comes out of the edge of the spine puller component edge, when it is inside the interspace, it perforates the end-plate and fixes itself there. This operation is also made by right and left laminectomy. Puller tools (46) are fixed to the retractor carrier wing (2). With the mechanism found at this point such as grasping and pulling, the puller tools are pulled upwards equally in terms of right and left sides, and this operation continues until the spines (41) reach their physiological positions via rontgen. From this point on, the fixing tool (35) is withdrawn inside and one of the puller apparatus is removed and then permanent insert (34) is mounted. Fixing tools (35) are placed inside both lower-upper end-plates in a way that they enter inside these. After completion of this operation, the spine puller component (46) found on the other side is removed in a similar manner. And permanent insert (34) is placed instead of it. At this point, after placement of the cover component (37) of one side, the interspace is filled with bone graft and the second cover component (37) is mounted to its place and closed. Therefore, two spines (41), which had slipped over each other, are brought to the position in which they had to be found, they are hanged via four fixing tools (35) which pass through the end-plates, bone fusion material is placed between them, and cover (37), which prevent the bone grafts getting out of the area, and which strengthen the inserts (34) are placed. This cover (37) also prevents micro movements of the inserts (34).

With the parts mounted on the retractor carrier wing body (2), fixation is made to the table from the table connection (16). The position of the retractor carrier wing (5) can be adjusted at desired points. The position of the retractor carrier wing (5) can be adjusted according to the table from its place of connection. The separator components (4) found on the separator component housing (rail) (3) on the retractor carrier wing (5) are positioned in the desired number. The separator components (4) are used in waist, neck and spine dislocations. The separator component (4) is mounted on the retractor carrier wing body (2) and its height can be adjusted from the separator component position adjustment point (17). It can be mounted and de-mounted in itself. At the front side of the separator edge (arm) (29), the separator edge z axis adjustment point (screw) (23) is found, which adjusts the position of the separating tool (24) upwards and downwards. Moreover, there is another separator edge y axis adjustment point (screws) (22), which provides opening and closing of the separating tool (24). A third is the separator edge y-z axis adjustment point (screw) (21), which provides adjustment of pandular movement (movement with angle) of the separator edge. In this way, adjustment can easily be made for entrance in a vertical position into the spine (41).

Separating tools (24) are formed in a structure that they are found on top of each other. This provides obtaining a very thin structure and eases entering into very thin interspaces. Moreover, the protrusions found on the separating tool (24) are formed in reverse structure with each other and this provides holding and separation of the spine (41) from two sides. With this system, which is placed on both sides, enters into the disc distance, and both excluding vertebra and muscles, the spines (41) can be moved in x-y axis equally from one side due to pandular movement. Moreover, lower corners can be reached by removing one of the separating tools (24) while the other is mounted or adjustment can be made by keeping the separating parts (24) in different depths.

Moreover, operations are performed in the known applications by constant parts stuck into corpus vertebra, which narrow the region of operation and has to be removed during operation. This makes the operation more difficult. Also, when rontgen monitoring is made, materials found here cause obstruction. While using microscope, a limited area is left for entrance of the relevant tools. The separating tool (24) parts can be removed and changed when desired: there is a releasing apparatus (automatic hand holder) (33) which provide release of the separator component (4) by giving pressure on it. This pressure is configured in a way that it would hold the relevant releasing point (20). When pressure is applied, it holds the part which provides its release. In this way, the separator edge (29) part can freely move and be mounted again. This operation can also be made alternatively. It can also be used in a constant structure.

The invention cannot be limited to the illustrative embodiments given under this section. Alternative embodiments that can be developed by persons skilled in the related art on basis of basic factors covered under scope of protections indicated under claims shall mean violation of the invention.

I claim:

1. A method of operating of a retractor used in spine surgery and which can be mounted to an operating table, the method comprising:
   forming at least two face-to-face retractor carrier wings which can be fixed on the operating table with at least one side arm, the side arm being openable and closable telescopically and being adjustable in a y-axis, the side arm being connected to at least one body connection arm, the body connection arm being adjustable;
   adjusting a position of the retractor carrier wings with a screwdriver at a desired position in x, y and z coordinates relative to the needs of the patient so as to separate muscles;
   adjustably axially position at least one separator component according to the patient and the operating table, the separator component having a mountable and demountable structure, the separator component being connected to a separating component housing formed on retractor wing bodies forming the retractor carrier wings;
   opening an operative field with the separator component;
   removal of a disc material from the diseased interspace between spine segments;
   bringing a spondylolistic spine to a desired position via spine puller components in which two of the spine puller components are placed from a left side to a right side into the diseased interspace so as to be fixed to the spondylolistic spine by perforating an endplate via a fixing tool protruding from an edge thereof while the spine puller components are in the diseased interspace;
   placing of two inserts into the diseased interspace after removing the spine puller components;
   fixing the two inserts to the spine from both upwardly and downwardly via a fixing tool protruding from inside the inserts; and
   covering an upper portion of the two inserts via a cover component.

2. The method of claim 1, further comprising:
   connecting a positioning apparatus to the two spine puller component; and
   pulling the spine puller components from a bearing point on the carrier wing body by rotating a rotation component of the positioning apparatus so as to bring the spine to the desired position.

3. The method of claim 2, further comprising:
   engaging the fixing tools to the spine in a vertical position through housings on the insert via an insert positioning and fixing component by pressure at one point; and
   demounting the fixing tools such that the insert is removed from its position via the positioning apparatus.

4. The method of claim 2, further comprising:
   fixing the fixing tools to the spine by mounting the fixing tools into the inserts via an assembly component of the positioning apparatus;
   covering an upper portion of the insert with the cover component, said cover component having a longitudinal structure;
   removing the cover component and pulling the fixing tools by turning the rotation component that is connected to an articulated connection on a position adjustment component from inside the positioning apparatus so as to release the inserts.

5. The method of claim 1, further comprising:
   covering upper and lower openings of the inserts in a sealed manner via the cover component, said cover component being fixed with fixing holes by being mounted to fixing points found in the inserts.

6. The method of claim 1, further comprising:
   adjusting a separating tool to desired adjustment points relative to the patient and the operating table, the separating tool having a telescopic structure so as to provide separation between the two spine segments in a vertical position.

* * * * *